US009334225B2

(12) United States Patent
Johnen et al.

(10) Patent No.: US 9,334,225 B2
(45) Date of Patent: May 10, 2016

(54) VINYL ESTERS OF ISONONANOIC ACID STARTING FROM 2-ETHYL HEXANOL, METHODS FOR THE PRODUCTION THEREOF AND USE THEREOF

(71) Applicant: Oxea GmbH, Oberhausen (DE)

(72) Inventors: Leif Johnen, Voerde (DE); Guido D. Frey, Riedstadt (DE); Matthias Eisenacher, Wesel (DE); Kristina Kockrick, Düsseldorf (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/413,429

(22) PCT Filed: Jun. 19, 2013

(86) PCT No.: PCT/EP2013/001803
§ 371 (c)(1),
(2) Date: Jan. 8, 2015

(87) PCT Pub. No.: WO2014/008977
PCT Pub. Date: Jan. 16, 2014

(65) Prior Publication Data
US 2015/0166456 A1 Jun. 18, 2015

(30) Foreign Application Priority Data
Jul. 13, 2012 (DE) .......................... 10 2012 014 396

(51) Int. Cl.
C07B 33/00 (2006.01)
C07C 67/04 (2006.01)
(Continued)

(52) U.S. Cl.
CPC . *C07C 67/04* (2013.01); *C07C 1/24* (2013.01); *C07C 45/50* (2013.01); *C07C 51/14* (2013.01);
(Continued)

(58) Field of Classification Search
CPC .......... C07C 67/04; C07C 1/24; C07C 45/50; C07C 51/14; C07C 51/21; C07C 51/235; C07C 67/10; C08E 220/68
USPC ........................................................ 554/124
See application file for complete search history.

(56) References Cited

U.S. PATENT DOCUMENTS 2,468,764 A   5/1949  Laurent
2,919,973 A   1/1960  Stillwell et al.
(Continued)

FOREIGN PATENT DOCUMENTS

CA   1081254 A1   7/1980
DE   950007 C     10/1956
(Continued)

OTHER PUBLICATIONS

International Preliminary Report on Patentability mailed Jan. 22, 2015.
(Continued)

*Primary Examiner* — Deborah D Carr
(74) *Attorney, Agent, or Firm* — Michael W. Ferrell

(57) ABSTRACT

Process for preparing the vinyl ester of isononanoic acid starting out from 2-ethylhexanol, characterized in that (a) 2-ethylhexanol is dehydrated in the presence of a catalyst to form octene; (b) the octene obtained in step a) is converted into an isononanoic acid having one more carbon atom; and (c) the isononanoic acid obtained in step b) is converted into the corresponding vinyl ester.

19 Claims, 1 Drawing Sheet

(51) Int. Cl.

| | | |
|---|---|---|
| *C07C 67/10* | (2006.01) | |
| *C07C 1/24* | (2006.01) | |
| *C07C 45/50* | (2006.01) | |
| *C07C 51/14* | (2006.01) | |
| *C07C 51/235* | (2006.01) | |
| *C07C 51/21* | (2006.01) | |
| *C08F 220/68* | (2006.01) | |

(52) U.S. Cl.
 CPC ............ *C07C 51/21* (2013.01); *C07C 51/235* (2013.01); *C07C 67/10* (2013.01); *C08F 220/68* (2013.01); *C07C 2521/04* (2013.01); *C07C 2521/08* (2013.01); *C07C 2523/755* (2013.01); *C07C 2527/173* (2013.01)

(56) References Cited

U.S. PATENT DOCUMENTS

| | | | |
|---|---|---|---|
| 3,527,809 | A | 9/1970 | Pruett et al. |
| 4,148,830 | A | 4/1979 | Pruett et al. |
| 4,247,486 | A | 1/1981 | Brewester et al. |
| 4,283,562 | A | 8/1981 | Billig et al. |
| 6,281,372 | B1 | 8/2001 | Wiese et al. |
| 6,423,856 | B1 | 7/2002 | Springer et al. |
| 7,799,945 | B2 | 9/2010 | Springer |
| 2014/0343310 | A1 | 11/2014 | Johnen et al. |

FOREIGN PATENT DOCUMENTS

| | | | |
|---|---|---|---|
| DE | 2604545 A1 | 8/1977 | |
| DE | 19908320 A1 * | 8/2000 | ............ C07C 45/50 |
| DE | EP 1057525 A2 * | 12/2000 | ................ B01J 8/06 |
| DE | 19940991 A1 | 3/2001 | |
| DE | 10010771 C1 | 5/2001 | |
| DE | 102012002282 A1 | 8/2013 | |
| EP | 0497340 A2 | 8/1992 | |
| EP | 1029839 A1 | 8/2000 | |
| EP | 1057525 A2 | 12/2000 | |
| EP | 1281701 A1 | 2/2003 | |
| EP | 1854778 A1 | 11/2007 | |
| EP | 2404671 A2 | 1/2012 | |
| GB | 313426 A | 6/1929 | |
| WO | 9322270 A1 | 11/1993 | |
| WO | 03029180 A1 | 4/2003 | |
| WO | 2011139360 A1 | 11/2011 | |
| WO | 2011139361 A1 | 11/2011 | |

OTHER PUBLICATIONS

International Search Report dated Jul. 26, 2013.

G. Hübner, "Vinylierung höherer Carbonsäuren an Katalysatorschmelzen", Fette, Seifen, Anstrichmittel, 1966, pp. 290-292, 68, 4.

Scharfe, G., "Convert butenes to high octane oligomers", Hydrocarbon Processing, Apr. 1973, pp. 171-173.

Robert L. Adelman, "The Interchange Reaction of Vinyl Acetate With Organic Acids", Journal Organic Chemistry, 1949, pp. 1057-1077, 14.

R.H. Friedlander et al., "Make Plasticizer Olefins Via N-Butene Dimerization", Hydrocarbon Processing, Feb. 1986, pp. 31-33.

* cited by examiner

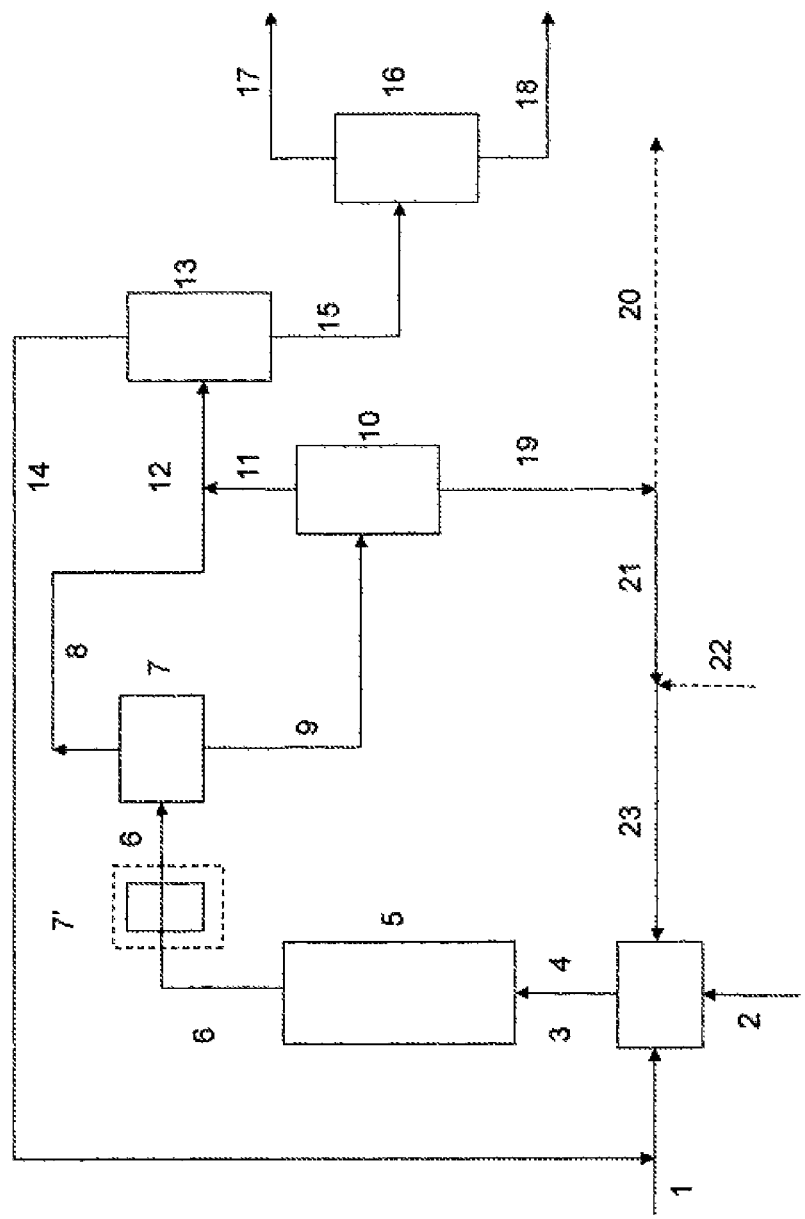

US 9,334,225 B2

VINYL ESTERS OF ISONONANOIC ACID STARTING FROM 2-ETHYL HEXANOL, METHODS FOR THE PRODUCTION THEREOF AND USE THEREOF

CLAIM FOR PRIORITY

This application is a national phase application of PCT/EP2013/001803 FILED Jun. 19, 2013 which was based on application DE 10 2012 014 396.6 FILED Jul. 13, 2012. The priorities of PCT/EP2013/001803 and DE 10 2012 014 396.6 are hereby claimed and their disclosures incorporated herein by reference.

TECHNICAL FIELD

The present invention relates to the vinyl ester of isononanoic acid starting out from 2-ethylhexanol, a process for preparing it by dehydration of 2-ethylhexanol, reaction of the resulting octene to form an isononanoic acid having one more carbon atom and subsequent reaction of the isononanoic acid produced in this way to form the corresponding vinyl ester, and also its use.

BACKGROUND

Vinyl esters of higher carboxylic acids are of some economic importance as comonomers. They can be used to modify the properties of polymers, for example polyvinyl chloride, polyvinyl acetate, polystyrene or polyacrylic esters. Thus, for example, the hydrolysis resistance of emulsion paints can be increased. Vinyl esters of higher carboxylic acids are also used for the production of adhesives. Vinyl esters based on 2-ethylhexanoic acid, isononanoic acid, lauric acid or the Versatic acids 911, 10 and 1519 from Shell are of industrial importance for these fields of use. These higher carboxylic acids can be obtained, for example, by oxidation of aldehydes which are prepared by the oxo process or by the Koch synthesis from the olefin, carbon monoxide and water. In the case of vinyl esters based on 2-ethylhexanoic acid, lauric acid or isononanoic acid, if the isononanoic acid consists predominantly of 3,5,5-trimethylhexanoic acid, uniform compounds are present, while in the case of vinyl esters of the Versatic acids 911, mixtures of highly branched carboxylic acids having from 9 to 11 carbon atoms, and in the case of vinyl esters of the Versatic acids 1519, mixtures of highly branched carboxylic acids having from 15 to 19 carbon atoms, are present in the vinyl ester. In the case of vinyl esters of Versatic acid 10, structurally different highly branched decanoic acids such as neodecanoic acids are derivatized.

Vinyl esters can be prepared by reaction of isononanoic acids with acetylene, preferably in the presence of zinc salts at temperatures of 200-230° C. (G. Hübner, Fette, Seifen, Anstrichmittel 68, 290 (1966); Ullmanns Encyklopädie der technischen Chemie, 4th edition, 1983, Verlag Chemie, volume 23, pages 606-607; EP 1 057 525 A2) or by the transvinylation reaction with a vinyl ester of another carboxylic acid, frequently vinyl acetate or vinyl propionate, in the presence of transition metal catalysts (Ullmanns Encyklopädie der technischen Chemie, 4th edition, 1983, Verlag Chemie, volume 23, pages 606-607; Adelmann, Journal Organic Chemistry, 1949, 14, pages 1057-1077; DE 199 08 320 A1, EP 0 497 340 A2, WO2011/139360 A1, WO2011/139361 A1).

The C4 fraction from the steam cracking of naphtha serves as raw material for the industrial preparation of isononanoic acid. Its availability compared to the C2 and C3 cracking products can be controlled by means of the conditions of the steam cracking and is guided by market circumstances. 1,3-butadiene is firstly removed from the C4 cracking product by extraction or by selective hydrogenation to form n-butenes. The C4 raffinate obtained, also referred to as raffinate I, contains predominantly the unsaturated butenes isobutene, 1-butene and 2-butene and also the hydrogenated products n-butane and isobutane. In the next step isobutene is removed from the raffinate I and the isobutene-free C4 mixture obtained is referred to as raffinate II.

In industrial production, the removal of isobutene is carried out using various processes in which the relatively high reactivity of isobutene in the raffinate I is exploited. The reversible proton-catalyzed molecular addition of water to form tert-butanol or the molecular addition of methanol to form methyl tert-butyl ether are known. Isobutene can be recovered again from these addition products by redissociation (Weissermel, Arpe, Industrielle Organische Chemie, VCH Verlagsgesellschaft, 3rd edition, 1988, pages 74-79).

Likewise, the butadiene-free C4 raffinate can be brought into contact with an acidic suspended ion exchanger at elevated temperature and under superatmospheric pressure. Isobutene oligomerizes to diisobutene, triisobutene and to a small extent to higher oligomers. The oligomers are separated off from the unreacted C4 compounds. Diisobutene or triisobutene can then be obtained in pure form from the oligomerization mixture by distillation. Codimer is formed to a small extent by dimerization of n-butenes with isobutene (Weissermel, Arpe, Industrielle Organische Chemie, VCH Verlagsgesellschaft, 3rd edition, 1988, page 77; Hydrocarbon Processing, April 1973, pages 171-173).

Diisobutene, either prepared by oligomerization of pure isobutene obtained by redissociation or obtained during the course of the work-up of a butadiene-free raffinate I, is subsequently converted into a C9 derivative which has one more carbon atom. Hydroformylation or the oxo process, in which diisobutene is converted by means of carbon monoxide and hydrogen in the presence of rhodium or cobalt catalysts into the corresponding aldehyde, is operated industrially. Since diisobutene contains predominantly the octenes 2,4,4-trimethyl-1-pentene and 2,4,4-trimethyl-2-pentene, the hydroformylation reaction gives the C9-aldehyde 3,5,5-trimethylhexanal as main constituent. Further C9 isomers which are present in small amounts are 3,4,4- and 3,4,5-trimethylhexanal and also 2,5,5-trimethylhexanal, 4,5,5-trimethylhexanal and 6,6-dimethylheptanal. Oxidation of this aldehyde mixture gives an industrially available isononanoic acid which usually has a content of 3,5,5-trimethylhexanoic acid of about 90% (Ullmanns Encyklopädie der technischen Chemie, 4th edition, 1975, Verlag Chemie, volume 9, pages 143-145; EP 1 854 778 A1).

Diisobutene can likewise be converted by means of hydrocarboxylation or the Koch reaction with carbon monoxide and water in the presence of sulphuric acid into the highly branched isononanoic acid 2,2,4,4-tetramethyl-1-pentanoic acid. Owing to the double alkyl branching on the carbon atom adjacent to the carboxyl group, this isononanoic acid is frequently also referred to as neononanoic acid. (Ullmanns Encyklopädie der technischen Chemie, 4th edition, 1975, Verlag Chemie, volume 9, pages 143-145).

The n-butenes present in the raffinate II after removal of isobutene are also converted industrially into butene oligomer mixtures from which the isomeric octenes are separated off and converted by hydrocarboxylation into the corresponding isononanoic acids (DE 199 08 320 A1; EP 1 029 839 A1). The oligomerization of n-butenes is carried out industrially over acidic catalysts such as zeolites or phosphoric acid on supports. This gives octenes which contain dimethylhexenes as main product. Further processes which may be mentioned are the DIMERSOL process and the OCTOL process. The DIMERSOL process is carried out using soluble nickel complex catalysts and leads to an octene mixture having a high proportion of 3- and 5-methylheptenes together with dimethylhexenes and n-octenes. In the OCTOL process, supported fixed-bed nickel catalysts are used and the octene mixture obtained has a low degree of branching (DE 199 08 320 A1, WO 03/029180, Hydrocarbon Processing, February 1986, pages 31-33). According to DE 199 08 320 A1, the respective, differently branched octene mixtures are converted by means of hydrocarboxylation into the corresponding isononanoic acids which are subsequently converted into the corresponding vinyl esters. Vinyl esters of isononanoic acids which are based on an octene mixture from the OCTOL process are suitable as plasticizing comonomer.

In view of the fact that the availability of octenes based on the C4 fraction from naphtha cracking is limited and depends on local site conditions, it is desirable to open up further octene sources on the basis of inexpensively available bulk products which can be transported in a simple way to the various sites. 2-Ethylhexanol is available at low cost as an industrial bulk product and can be marketed widely without problems. 2-Ethylhexanol is, as is known, prepared industrially by hydroformylation or oxo reaction of propylene to form n-butyraldehyde with subsequent alkali-catalyzed aldol condensation to form 2-ethylhexenal and subsequent total hydrogenation to 2-ethylhexanol (Ullmanns Encyklopädie der technischen Chemie, 4th edition, 1974, Verlag Chemie, volume 7, pages 214-215).

The use of 2-ethylhexanol for preparing an octene mixture which is processed by dehydration, hydroformylation and hydrogenation to give an isononanoic mixture, is briefly described in WO 03/029180 A1. Here, setting of the viscosity of the isomeric alkyl phthalates which are obtained by esterification of isomeric nonanols with phthalic acid or phthalic anhydride is the main focus. Information as to how to convert the dehydration products of 2-ethylhexanol into isononanoic acid is not given.

The utilization of 2-ethylhexanol as octene source makes it possible to provide the vinyl ester of isononanoic acid on the basis of propylene and reduces the dependence on the availability of octenes based on butene.

SUMMARY OF INVENTION

The present invention accordingly provides a process for preparing the vinyl ester of isononanoic acid starting out from 2-ethylhexanol. The process is characterized in that
(a) 2-ethylhexanol is dehydrated in the presence of a catalyst to form octene;
(b) the octene obtained in step a) is converted into an isononanoic acid having one more carbon atom; and
(c) the isononanoic acid obtained in step b) is converted into the corresponding vinyl ester.

The present invention likewise provides the vinyl ester of isononanoic acid starting out from 2-ethylhexanol, which can be obtained by
(a) dehydrating 2-ethylhexanol in the presence of a catalyst to form octene;
(b) converting the octene obtained in step a) into an isononanoic acid having one more carbon atom; and
(c) converting the isononanoic acid obtained in step b) into the corresponding vinyl ester.

DETAILED DESCRIPTION

The dehydration of 2-ethylhexanol can be carried out either in the liquid phase or in the gas phase over a catalyst suitable for this purpose. The dehydration is preferably carried out in the gas phase at temperatures in the range from 200 to 450° C., preferably from 250 to 380° C., using conventional reactors in the presence of acidic heterogeneous catalysts such as aluminium oxide in its various modifications, nickel deposited on aluminium oxide or phosphoric acid deposited on silicon dioxide or aluminium oxide. Such heterogeneous catalysts suitable for dehydration are known from the prior art (GB 313426, U.S. Pat. Nos. 2,468,764, 2,919,973) and are commercially available as, for example, A13996 from BASF SE. U.S. Pat. No. 2,919,973 is concerned with the dehydration of 2-ethylhexanol over a heterogeneous aluminium oxide catalyst at temperatures of about 350° C. and a space velocity over the catalyst of from 2.4 to 2.8 litres of 2-ethylhexanol per litre of catalyst and hour. However, the prior art gives no information on the isomer distribution in the octene mixture obtained.

The reactor used in the process of the invention for the dehydration of 2-ethylhexanol can contain not only the catalyst bed but also further packing elements or internals, for example Raschig rings, saddles, Pall rings, filter plates or column trays. If packing elements are used, they are preferably installed above the catalyst bed in order to reduce the dead volume. If dehydration is carried out in the liquid phase, stirring devices, internals and packing elements can be dispensed with, so that only the dehydration catalyst is present in the reaction vessel. In the preferred mode of operation, 2-ethylhexanol is heated in an upstream vaporizer and passed in gaseous form over the catalyst bed, optionally using an inert carrier gas such as nitrogen, carbon dioxide or noble gases. The space velocity V/Vh over the heterogeneous catalyst can vary over a wide range and is generally from 0.2 to 3.5 litres of 2-ethylhexanol per litre of catalyst an hour. The reaction mixture taken off from the dehydration zone is subsequently condensed. Due to the eliminated water, an aqueous phase is formed and this is separated from the organic olefin phase by simple phase separation. The octene obtained is a mixture of structurally isomeric octenes having the singly branched octenes 2-ethyl-1-hexene and cis/trans 3-methyl-3-heptene and cis/trans 3-methyl-2-heptene as main components. Appreciable amounts of di-C8-ethers are not formed.

The octene obtained after removal of the eliminated water is subsequently converted without further purification or advantageously after purification by distillation into the corresponding isononanoic acid.

In one embodiment, the octene obtained is reacted with carbon monoxide and hydrogen in the hydroformylation reaction or oxo process. The mixture of carbon monoxide and hydrogen which is used is also referred to as synthesis gas.

The hydroformylation reaction is carried out in a homogeneous reaction system. The term homogeneous reaction system refers to a homogeneous solution composed essentially of solvent, if added, catalyst, olefinically unsaturated compound and reaction product. The relatively high-boiling condensation compounds of the aldehydes to be prepared, in particular the trimers of the aldehydes to be prepared, which are obtained as by-products in the hydroformylation and also their mixtures with the isononanal to be prepared have been found to be particularly effective solvents, so that a further addition of solvent is not absolutely necessary. However, in some cases an addition of solvent has been found to be advantageous. As solvents, use is made of organic compounds in which the starting material, reaction product and catalyst are soluble. Examples of such compounds are aromatic hydrocarbons such as benzene and toluene or the isomeric xylenes and mesitylene. Other solvents which can be used are paraffin oil, cyclohexane, n-hexane, n-heptane or n-octane, ethers such as tetrahydrofuran, ketones or Texanol® from Eastman. The proportion of solvent in the reaction medium can be varied over a wide range and is usually from 20 to 90% by weight, preferably from 50 to 80% by weight, based on the reaction mixture. However, the hydroformylation of the octene can also be carried out without addition of solvent.

The hydroformylation reaction is carried out in a homogeneous organic phase in the presence of at least one transition metal compound of group VIII of the Periodic Table of the Elements. The reaction can be carried out either in the presence or in the absence of complexing organoelement compounds which act as complexing ligands.

If the hydroformylation reaction is carried out in the presence of complexing ligands, the use of organophosphorous compounds as organoelement compounds is useful. Such complexes and their preparation are known (U.S. Pat. Nos. 3,527,809 A, U.S. Pat. No. 4,148,830 A, U.S. Pat. No. 4,247, 486 A, U.S. Pat. No. 4,283,562 A). They can be used as uniform complexes or also as a mixture of various complexes. The transition metal concentration in the reaction medium extends over a wide range from about 1 to about 1000 ppm by weight and is preferably from 10 to 700 ppm by weight and in particular from 25 to 500 ppm by weight, in each case based on the homogeneous reaction mixture. As catalyst, it is possible to employ the stoichiometric transition metal complex. However, it has been found to be advantageous to carry out the hydroformylation in the presence of a catalyst system composed of transition metal complex and free complexing ligand which no longer undergoes complexation with the transition metal. The free complexing ligand can be the same one as that in the transition metal complex, but it is also possible to use complexing ligands different from this. Preferred complexing ligands include triarylphosphines such as triphenylphosphine, trialkylphosphines such as tri(cyclohexyl)phosphine, alkylphenylphosphines, organic phosphites or diphosphites. The molar ratio of transition metal to complexing ligand is generally from 1:1 to 1:1000 but can also be higher. Preference is given to using the transition metal and the complexing ligand in a molar ratio of from 1:3 to 1:500 and in particular from 1:50 to 1:300.

The hydroformylation reaction in the presence of complexing ligands is frequently also referred to as modified variant, which is usually carried out at temperatures of from 50 to 180° C., preferably from 100 to 160° C., and total pressures of from 0.2 to 30 MPa, preferably from 1 to 20 MPa.

The hydroformylation reaction can likewise be carried out in the absence of complexing ligands by the unmodified variant. Such transition metal catalysts which, for example, are not modified with phosphines or phosphites and their suitability as catalyst for hydroformylation are known from the literature and are referred to as unmodified transition metal catalysts. It is assumed in the technical literature that the transition metal compound $HM(CO)_4$ is the catalytically active transition metal species in the unmodified transition metal catalysis, although this has not been proven unambiguously because of the many chemical mechanisms proceeding side by side in the reaction zone.

As transition metals of group VIII of the Periodic Table of the Elements, preference is given to using cobalt, rhodium, iridium, nickel, palladium, platinum, iron or ruthenium and in particular cobalt or rhodium. The modified or unmodified transition metal catalyst is formed under the conditions of the hydroformylation reaction from the transition metal compounds used, e.g. their salts such as chlorides, nitrates, sulphates, acetates, pentanoates, 2-ethylhexanoates or isononanoates, their chalcogenides, such as oxides or sulphides, their carbonyl compounds such as $M_2(CO)_8$, $M_4(CO)_{12}$, $M_6(CO)_{16}$, $M_2(CO)_9$, $M_3(CO)_{12}$, their organic transition metal compounds such as carbonyl-acetylacetonates or cyclooctadienyl-acetates or -chlorides, in the presence of carbon monoxide/hydrogen mixtures. Here, the transition metal compound can be used as solid or advantageously in solution. As transition metal compound which is used as catalyst precursor, it is possible to use, in particular, rhodium isononanoate, rhodium acetate, rhodium 2-ethylhexanoate or cobalt isononanoate, cobalt acetate or cobalt 2-ethylhexanoate, or $Co_2(CO)_8$, $Co_4(CO)_{12}$, $Rh_2(CO)_8$, $Rh_4(CO)_{12}$ or $Rh_6(CO)_{16}$ or cyclopentadienylrhodium compounds, rhodium acetylacetonate or dicarbonylrhodium acetylacetonate. Preference is given to using rhodium oxide and in particular rhodium acetate, rhodium 2-ethylhexanoate and rhodium isononanoate.

However, it is also possible firstly to preform the transition metal catalyst in a precarbonylation stage and subsequently introduce it into the actual hydroformylation stage. The conditions of preformation generally correspond to the hydroformylation conditions.

Since the use of transition metal catalysts which have not been modified with complexing ligands generally requires a lower transition metal content, the reaction is generally carried out using an amount of transition metal of from 1 to 100 ppm, preferably from 2 to 30 ppm, based on the octene used. Very particular preference is given to using rhodium or cobalt in an amount of from 2 to 30 ppm, preferably from 5 to 10 ppm, in each case based on the octene used.

The reaction of the octene with hydrogen and carbon monoxide to form isononanal according to the unmodified variant is advantageously carried out at relatively high pressures in the range from 5 to 70 MPa, preferably from 5 to 60 MPa and in particular from 10 to 30 MPa. Suitable reaction temperatures are in the range from 50 to 180° C., preferably from 50 to 150° C. and in particular from 100 to 150° C.

The composition of the synthesis gas, i.e. the proportions of carbon monoxide and hydrogen in the gas mixture, can vary within wide limits. In general, mixtures in which the molar ratio of carbon monoxide to hydrogen is from 5:1 to 1:5 are used. This ratio is usually 1:1 or deviates only slightly from this value. The olefinic compound can be introduced as such or in solution into the reaction zone. Suitable solvents are ketones such as acetone, methyl ethyl ketone, acetophenone, lower aliphatic nitriles such as acetonitrile, propionitrile or benzonitrile, dimethylformamide, linear or branched saturated aliphatic monohydroxy compounds such as methanol, ethanol, propanol and isopropanol, aromatic hydrocarbons such as benzene or toluene and saturated cycloaliphatic hydrocarbons such as cyclopentane or cyclohexane.

The hydroformylation stage can be carried out either batchwise or continuously. The desired aldehydes are isolated from the crude hydroformylation product by conventional methods, for example by distillation. Isononanal and further volatile components are taken off as overhead products and, if required, subjected to a further fine purification.

The amounts of transition metal used are obtained in the distillation residue and are, optionally after addition of fresh transition metal compound and removal of part of the aldehyde condensation products formed during the reaction, recirculated to the reaction zone.

The resulting mixture of isomeric isononanals is purified, advantageously by distillation, and subsequently converted by oxidation into the corresponding isononanoic acid, preferably by oxidation in the liquid phase, although other process variants such as oxidation in the gas phase are not ruled out. Suitable oxidants are customary compounds suitable for the oxidation of aliphatic aldehydes, e.g. oxygen, oxygen-containing gas mixtures, ozone, ozone-containing gas mixtures, peroxides, peracids, metal salts of peracids or transition metals in high oxidation states, for example potassium permanganate or manganese dioxide. Owing to the ready availability, molecular oxygen or gas mixtures containing molecular oxygen are advantageously used as oxidant. Further constituents of such gas mixtures are inert gases, e.g. nitrogen, noble gases and carbon dioxide. The proportion of inert constituents in the oxygen-containing gas mixture is up to 90% by volume, in particular from 30 to 80% by volume. The preferred oxidant is oxygen or air.

The oxidation can be carried out either with addition of catalyst or in the absence of catalysts. Suitable catalysts are transition metals or compounds of transition metals which can be added in small amounts, for example from 0.1 to 5 ppm, calculated as transition metal and based on aldehyde used, for example titanium, vanadium, chromium, molybdenum, manganese, iron, cobalt, nickel, ruthenium, rhodium, palladium or copper. Such a way of carrying out the process is described, for example, in DE 100 10 771 C1 or DE 26 04 545 A1.

The reaction can likewise be carried out in the presence of alkali metal or alkaline earth metal salts of weak acids. Particularly in the oxidation of α-branched aldehydes, in which the carbon atom adjacent to the carbonyl carbon bears the branch, the prior art recommends the presence of small amounts of alkali metal carboxylates for improving the selectivity (DE 950 007, DE 100 10 771 C1). A combination of alkali metal carboxylates or alkaline earth metal carboxylates with transition metal compounds, as described in EP 1 854 778 A1, can also be used.

In the oxidation of isononanal, which according to the process of the invention is prepared from 2-ethylhexanol via dehydration and hydroformylation to form the corresponding octene, the presence of alkali metal carboxylates or alkaline earth metal carboxylates is advisable, generally in an amount of from 1 to 30 mmol, preferably from 1 to 15 mmol and in particular from 1 to 8 mmol, per mol of aldehyde, calculated as alkali metal or alkaline earth metal.

It is not necessary to use the alkali metal or alkaline earth metal carboxylates as a uniform compound. It is likewise possible to use mixtures of these compounds, but isononanoates are advantageously used. However, preference is given to using uniform compounds, for example lithium, potassium, sodium, calcium or barium isononanoate.

In general, a solution containing alkali metal or alkaline earth metal isononanoates is produced by neutralization of an aqueous solution containing the alkali metal or alkaline earth metal compound with an excess of isononanoic acid and this solution is added to the isononanal to be oxidized. Particularly suitable alkali metal or alkaline earth metal compounds are the hydroxides, carbonates or hydrogencarbonates.

However, it is also possible to generate the alkali metal or alkaline earth metal isononanoates in the reaction mixture by adding alkali metal or alkaline earth metal compounds which are converted under the reaction conditions into the isononanoates. For example, it is possible to use alkali metal or alkaline earth metal hydroxides, carbonates, hydrogen carbonates or oxides in the oxidation stage. They can be added either in solid form or as aqueous solution.

The reaction with the oxidant, preferably with oxygen or oxygen-containing gases, is carried out in the temperature range from 20 to 100° C. Preference is given to working at from 20 to 80° C., in particular from 40 to 80° C. The temperature conditions, constant or variable temperature, can be matched to the individual requirements of the starting material and the circumstances of the reaction.

The reaction of the reactants is preferably carried out under atmospheric pressure. However, the use of superatmospheric pressure is not ruled out. The reaction is usually carried out in a range from atmospheric pressure to 1.5 MPa, preferably at from atmospheric pressure to 0.8 MPa.

The reaction time required to convert the isononanal into the corresponding isononanoic acid depends, inter alia, on the reaction temperature and the ratio of the reactants. It is normally from 30 minutes to 20 hours, in particular from 2 to 8 hours.

Isononanal can be used either as such or dissolved in a solvent which is inert under the reaction conditions. Examples of suitable solvents are ketones such as acetone, esters, e.g. ethyl acetate, hydrocarbons, e.g. toluene, and nitrohydrocarbons such as nitrobenzene. The concentration of the aldehyde is limited by its solubility in the solvent.

The oxidation step can be carried out batchwise or continuously. Recirculation of unreacted reaction participants is possible in both cases.

The isononanoic acid obtained starting out from 2-ethylhexanol with subsequent hydroformylation and oxidation is a mixture of positionally isomeric aliphatic C9-monocarboxylic acids with isononanoic acids which are unbranched or singly branched in the a position as main components.

According to gas-chromatographic analysis in accordance with DIN 51405 (% by area), 4-methyloctanoic acid, 6-methyloctanoic acid, 2,5-dimethylheptanoic acid, 2,3-dimethylheptanoic acid, 3-ethylheptanoic acid, 2-ethylheptanoic acid and 2-ethyl-4-methylhexanoic acid are present as main components together with small amounts of 2-propyl-3-methylpentanoic acid and 2-methyloctanoic acid. Small amounts of nonanoic acid are likewise present.

The isononanoic acid prepared by the process of the invention via the hydroformylation and oxidation reactions is characterized in that the main components 4-methyloctanoic acid, 6-methyloctanoic acid, 2,5-dimethylheptanoic acid, 2,3-dimethylheptanoic acid, 3-ethylheptanoic acid, 2-ethylheptanoic acid and 2-ethyl-4-methylhexanoic acid make up a total of at least 80 mol % of the total content of positionally isomeric aliphatic C9-monocarboxylic acids.

The pure isononanoic acid is obtained from the crude acid mixture obtained after the oxidation by means of distillation under customary conditions. The distillation residue containing the alkali metal or alkaline earth metal isononanoates and possibly transition metals is separated off and can, optionally after addition of fresh alkali metal or alkaline earth metal isononanoates or alkali metal or alkaline earth metal compounds which are converted under the reaction conditions into the isononanoates and also optionally fresh transition metal compounds, be recirculated to the feed aldehyde.

In an embodiment of the process of the invention which has been found to be useful, isononanal is placed in a suitable reactor, e.g. in a tube reactor which is provided with an inflow tray and optionally contains packing elements, and the oxygen or the oxygen-containing gas mixture is passed from below through the aldehyde.

In a further embodiment, a trickle tower containing packing elements is used as reactor. The aldehyde is allowed to trickle down over the packing and oxygen or an oxygen-containing gas mixture is simultaneously fed into the tower in cocurrent or countercurrent.

The octene obtained by dehydration of 2-ethylhexanol can likewise be converted into a mixture of highly branched isononanoic acids by hydrocarboxylation using carbon monoxide and water according to the Koch reaction (Weissermel, Arpe, Industrielle Organische Chemie, VCH Verlagsgesellschaft, 3rd edition, 1988, pages 150-152; J. Falbe, Carbon Monoxide in Organic Synthesis, Springer Verlag Berlin, Heidelberg, N.Y., 1970, pages 127-135). The reaction is carried out in the presence of strongly acidic protic catalysts such as sulphuric acid, hydrogen fluoride or phosphoric acid, frequently also in admixture with Lewis acids such as boron trifluoride or antimony pentafluoride. A suitable catalyst system for the hydrocarboxylation of olefins is a mixture of boron trifluoride and phosphoric acid in a molar ratio of 1.5:1 and is known from WO 93/22270 A1. According to EP 1 281 700 A1, this molar ratio can vary over a range from 0.5:1 to 5.0:1. The reaction of octene is generally carried out at temperatures in the range from 60 to 140° C. and at a carbon monoxide pressure of from 5 to 12 MPa in the presence of water in an amount of from 8 to 30% by weight, based on the amount of catalyst used.

After the reaction is complete, the organic phase is separated from the aqueous phase and purified by scrubbing with water. According to mechanistic concepts, a tertiary carbenium ion is firstly formed in the olefin skeleton by molecular addition of a proton under the strongly acidic reaction conditions and the carbon monoxide is added onto this to form an acylium cation which is subsequently saturated with water. In the hydrocarboxylation of octene, this reaction sequence forms an isononanoic acid having tertiary structural isomers which bear two α,α-alkyl radicals on the carbon atom adjacent to the carboxyl group and have a neo structure.

The isononanoic acid prepared according to the invention from 2-ethylhexanol is subsequently converted into the corresponding vinyl ester. This can be effected by, for example, reaction of the isononanoic acid with acetylene, preferably in the presence of zinc salts, at temperatures of 200-230° C. (G. Hübner, Fette, Seifen, Anstrichmittel 68, 290 (1966), Ullmanns Encyklopädie der technischen Chemie, 4th edition, 1983, Verlag Chemie, volume 23, pages 606-607; EP 1 057 525 A2).

It is likewise possible to subject the isononanoic acid obtained in this way to a transvinylation reaction with a vinyl ester of another carboxylic acid:

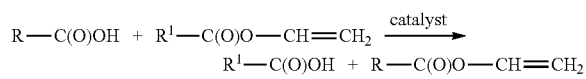

where R is C8 and $R^1$ is frequently methyl or ethyl, so that, for example, vinyl acetate or vinyl propionate is used as transvinylation reagent (Ullmanns Encyklopädie der technischen Chemie, 4th edition, 1983, Verlag Chemie, volume 23, pages 606-607). To push the chemical equilibrium in the direction of the desired vinyl ester, an excess of the transvinylation reagent $R^1$—C(O)O—CH=$CH_2$ is frequently used and the carboxylic acid formed is simultaneously removed from the reaction mixture. The continuous or semicontinuous embodiment of the process can, for example, be configured as a reactive distillation (EP 0 497 340 A2) or as a bubble column with superposed column, downstream of which a rectification column and a stripping column are additionally installed (WO 2011/139360 A1 and WO 2011/139361 A1).

However, it is also possible to carry out the transvinylation reaction continuously without removal of a reactant and to separate the resulting reaction mixture into the individual components in a separate work-up section, a procedure which is described in DE 10 2012 002282 A1. In this procedure, the transvinylation reaction can be carried out either at atmospheric pressure or under superatmospheric pressure, generally up to a pressure of 15 MPa, preferably from 0.5 to 8 MPa and in particular from 0.8 to 2 MPa. Reactions at a temperature of from 90 to 140° C. and at a pressure of from 0.8 to 2 MPa have been found to be particularly suitable. However, very high space-time yields of the desired vinyl ester of isononanoic acid are likewise achieved at atmospheric pressure and in particular at a reaction temperature of from 60 to 150° C.

A suitable reaction vessel is a tube reactor such as a flow tube arranged in any way, for example as a vertically upright or horizontal flow tube or a multiply coiled flow tube. The tube reactor can be operated as an empty tube but can likewise contain packing elements or internals, for example Raschig rings, saddles, Pall rings, helices, baffles or static mixers or mixer packings. Static mixing elements are commercially available and are marketed, for example, as Sulzer mixers or Kenicks mixers with specific product lines for the mixing of liquids having different viscosities. The tube reactor can likewise be provided with a circulation pump and optionally with a heat exchanger.

The transvinylation reaction can likewise be carried out continuously in a stirred vessel or in a cascade of stirred vessels under atmospheric pressure or under superatmospheric pressure. The isononanoic acid and the transvinylation reagent $R^1$—C(O)O—CH=$CH_2$ are fed in continuously, either separately or as a mixture, and the reaction mixture present in the steady state is discharged continuously. The continuous reaction can likewise be carried out in conventional reactor designs, for example in a loop reactor using heat convection or in a multichamber reactor. The reaction vessel can likewise be configured as a cylindrical reactor which has an axially arranged nozzle for introduction of the liquid, catalyst-containing mixture of isononanoic acid and the transvinylation reagent $R^1$—C(O)O—CH=$CH_2$ and additionally contains an axially arranged guide tube for generating forced internal flow.

A space velocity V/Vh of a previously produced mixture of the transvinylation reagent and the isononanoic acid through the reaction vessel of from 0.4 to 7.0 $h^{-1}$, preferably from 0.7 to 6.2 $h^{-1}$, based on the reactor volume and time, has been found to be advantageous. If both starting materials are introduced separately but simultaneously into the reaction vessel, the space velocity V/Vh of the transvinylation reagent through the reaction vessel is from 0.02 to 6.0 $h^{-1}$ and that of the isononanoic acid is from 0.1 to 6.7 $h^{-1}$, in each case based on the reactor volume and time.

It is likewise possible to carry out the transvinylation reaction batchwise in a closed reaction vessel. Here, it has been found advantageous to carry out the process at temperatures of from 60 to 150° C. and at pressures from autogenous pressure to 5 MPa. The desired pressure can, for example, be set by injection of an inert gas such as nitrogen or noble gases.

As transvinylation reagent $R^1$C(O)O—CH=$CH_2$, preference is given to using vinyl acetate in which $R^1$ is methyl or vinyl propionate in which $R^1$ is ethyl. However, vinyl esters of higher carboxylic acids, e.g. vinyl laurate in which $R^1$ is undecyl, can also be used when their use appears to be advantageous for the subsequent work-up of the reaction mixture. The reaction mixture obtained is usually purified by distillation.

Based on usage of isononanoic acid, the transvinylation reagent $R^1$—C(O)O—CH=$CH_2$ can be used in a molar ratio of from 0.1:1 to 10:1, preferably from 0.2:1 to 5:1. The amount thereof likewise depends on the physical properties of the starting materials and the reactants formed and then on the way in which the reaction mixture can be worked up as advantageously as possible.

Vinyl acetate has been found to be an advantageous transvinylation reagent because of its availability at low cost, its boiling point and the boiling point of the acetic acid formed in the transvinylation reaction. The reaction mixture is usually worked up by distillation and excess vinyl acetate, acetic acid formed and the desired vinyl ester of isononanoic acid are taken off as volatile components and fractionated further. Isononanoic acid together with the transvinylation catalyst remain in the residue. The catalyst-containing residue is, after optional discharge of a high boiler-container substream, recirculated to the transvinylation reaction, optionally after addition of fresh catalyst or fresh ligands.

It is likewise possible to use vinyl acetate in a molar excess of up to 0.1:1, preferably up to 0.2:1, based on the moles of isononanoic acid used. This enables the outlay for separating off vinyl acetate to be reduced.

The acetic acid liberated in the transvinylation reaction with vinyl acetate can, after purification, be used for subsequent derivatization reactions, for example for preparing vinyl acetate by reaction with ethylene and oxygen over solid, palladium-containing supported catalysts (Weissermel, Arpe, Industrielle Organische Chemie, VCH Verlagsgesellschaft, 3rd edition, 1988, pages 244-247).

The esterification of the acetic acid obtained by means of lower aliphatic alcohols such as methanol, ethanol, n-propanol, isopropanol, n-butanol or isobutanol gives the corresponding acetate esters such as n-propyl acetate, isopropyl acetate, n-butyl acetate or isobutyl acetate. The esterification of acetic acid by means of lower aliphatic alcohols is known per se (Ullmanns Encyklopädie der technischen Chemie, 4th edition, 1983, Verlag Chemie GmbH, volume 11, pages 68-70; volume 19, pages 457-458). Further illustrative derivatives which can be prepared from the acetic acid liberated by methods known per se are acetyl halides, amides, carboxylic anhydrides, chloroacetic acids or ethanol.

Suitable transvinylation catalysts are compounds of the transition metals of the platinum group, viz. ruthenium, osmium, rhodium, iridium, palladium and platinum, in particular palladium and ruthenium, which can be used modified by means of monodentate or polydentate organonitrogen or organophosphorous ligands or in modified form. The total concentration of the transition metal or transition metals, if a mixture thereof is used, is generally from 0.005 to 1 mol %, preferably from 0.01 to 0.5 mol % and in particular from 0.02 to 0.25 mol %, in each case based on the starting compound used in a substoichiometric amount. Ruthenium compounds are, for example, used in unmodified form and palladium compounds are frequently modified with 2,2'-bipyridyl or 1,10-phenanthroline or in unmodified form together with an alkali metal compound such as lithium acetate and a redox-active transition metal, for example divalent copper in the form of halides.

The vinyl isononanoate obtained can be used in copolymers. It is suitable as comonomer in polyvinyl acetate, polyvinyl chloride, polystyrene or polyacrylic esters, which advantageously influence the hydrolysis resistance and moisture absorption of paints.

In the following examples, the preparation of isononanoic acid starting out from 2-ethylhexanol and its conversion into the vinyl ester are described.

EXAMPLES

I. Dehydration of 2-ethylhexanol

A fused silica tube which had a length of 1.3 metre and a diameter of 0.03 metre and in which the heated zone extended over 1.1 metre was used for the dehydration. The fused silica tube was charged with 250 ml of the acid catalyst Al 3996 from BASF SE in the form of 3×3 millimetre pellets. The dead volume was filled with glass rings.

2-Ethylhexanol was vaporized in an upstream vaporizer and conveyed with the aid of a stream of nitrogen as carrier gas at atmospheric pressure over the catalyst bed at a temperature of 350° C. and a space velocity of 0.5 litre per litre of catalyst volume and hour. The reaction mixture obtained was condensed in a downstream collection vessel and the aqueous phase was separated off. The organic phase obtained had the following composition determined by gas chromatography (% by area, in accordance with DIN 51405):

| First fraction/C4-C7-hydrocarbons | 0.3 |
| Other C8-olefins | 9.6 |
| 2-Ethyl-1-hexene | 7.6 |
| cis-3-Methyl-3-heptene | 14.6 |
| trans-3-Methyl-3-heptene | 28.8 |
| cis-3-Methyl-2-heptene | 16.2 |
| trans-3-Methyl-2-heptene | 23.9 |
| n-Octenes | 0.8 |
| Final fraction | 0.1 |

II. Hydroformylation of the Octene Obtained in Step I.

The crude octene obtained from step I was hydroformylated in the presence of 5 ppm of rhodium, added in the form of a solution of rhodium 2-ethylhexanoate in 2-ethylhexanol and based on octene used, at a temperature of 140° C. and a synthesis gas pressure of 19 MPa over a period of three hours. The molar composition of the synthesis gas was 1 mol of hydrogen to 1 mol of carbon monoxide. The crude hydroformylation product obtained had the following composition determined by gas chromatography (% by area, in accordance with DIN 51405):

| First fraction | 0.1 |
| C8-hydrocarbons | 8.5 |
| Intermediate fraction | 0.2 |
| Isononanal | 88.1 |
| n-Nonanal | 1.4 |
| Final fraction | 1.7 |

The results of further hydroformylation experiments using an octene obtained by dehydration of 2-ethylhexanol are shown in Table 1 below. Before use, the crude octene was distilled via a Claisen bridge to separate off the final fraction at a temperature at the top of 119-122° C. and atmospheric pressure. The starting octenes and the reaction products obtained were analysed by gas chromatography (reported in % by area, in accordance with DIN 51405).

TABLE 1

Hydroformylation of octenes obtained by dehydration of 2-ethylhexanol

| | Example | |
| --- | --- | --- |
| | IIa | IIb |
| Starting material | distilled | distilled |
| GC analysis of starting material (%) | | |
| First fraction/C4-C7-hydrocarbons | 0.3 | 0.4 |
| Other C8-Olefins | 5.9 | 7.7 |
| 2-Ethyl-1-hexene | 9.3 | 9.2 |
| cis-3-Methyl-3-heptene | 15.2 | 15.0 |
| trans-3-Methyl-3-heptene | 27.4 | 27.1 |
| cis-3-Methyl-2-heptene | 16.1 | 15.6 |

TABLE 1-continued

Hydroformylation of octenes obtained by dehydration of 2-ethylhexanol

|  | Example | |
|---|---|---|
|  | IIa | IIb |
| trans-3-Methyl-2-heptene | 25.2 | 24.7 |
| n-Octenes | 0.5 | 0.2 |
| Final fraction | 0.1 | 0.1 |
| Experimental conditions | | |
| Rh concentration [ppm], based on octene used | 20 | 10 |
| Pressure [MPa] | 19 | 27 |
| Temperature [° C.] | 140 | 140 |
| Reaction time [h] | 2 | 2 |
| GC analysis of product (%) | | |
| First fraction | 0.1 | 0.1 |
| C8-hydrocarbons | 2.5 | 1.1 |
| Intermediate fraction | 0.3 | 0.1 |
| Isononanals | 90.8 | 94.7 |
| n-Nonanal | 2.0 | 1.4 |
| Final fraction | 4.3 | 2.6 |

The hydroformylation experiments carried out using triphenylphosphine as complexing ligand and the octene obtained by dehydration of 2-ethylhexanol are shown in Table 2 below. Undistilled material was used. The starting octenes and the reaction products obtained were analysed by gas chromatography (reported in % by area, in accordance with DIN 51405).

TABLE 2

Hydroformylation of octenes obtained by dehydration of 2-ethylhexanol, addition of triphenylphosphine

|  | Example | | | |
|---|---|---|---|---|
|  | IIc | IId | IIe | IIf |
| Starting material | un-distilled, crude | un-distilled, crude | un-distilled, crude | un-distilled, crude |
| GC analysis of starting material (%) | | | | |
| C4-C7-hydrocarbons | 0.3 | 0.3 | 0.3 | 0.4 |
| Other C8-olefins | 19.1 | 19.1 | 19.1 | 11.6 |
| 2-Ethyl-1-hexene | 7.9 | 7.9 | 7.9 | 8.6 |
| 3-Methyl-3-heptene | 36.5 | 36.5 | 36.5 | 40.0 |
| 3-Methyl-2-heptene | 36.2 | 36.2 | 36.2 | 39.3 |
| Final fraction | <0.01 | <0.01 | <0.01 | 0.1 |
| Experimental conditions | | | | |
| Rh concentration [ppm], based on octene used | 10 | 10 | 10 | 10 |
| Equivalents of TPP | 3 | 50 | 100 | 3 |
| Pressure [MPa] | 18 | 27 | 18 | 14 |
| Temperature [° C.] | 140 | 140 | 140 | 160 |
| Reaction time [h] | 1 | 2 | 1 | 2 |
| GC analysis of product (%) | | | | |
| First fraction | 0.1 | 0.1 | 0.1 | 0.1 |
| C8-hydrocarbons | 52.2 | 70.9 | 81.7 | 14.1 |
| Intermediate fraction | 0.8 | 0.1 | 0.1 | 1.9 |
| Isononanals | 45.7 | 28.3 | 17.6 | 76.1 |
| n-Nonanal | 0.5 | 0.1 | 0.1 | 0.5 |
| Final fraction | 0.7 | 0.4 | 0.4 | 7.3 |

III. Oxidation of the Isononanal Obtained in step II. to Isononanoic Acid

Low boilers and unreacted olefin were firstly separated off as overhead product from the isononanal obtained in Example IIa in a 24 plate column at 200 hPa, a temperature at the bottom of 120° C. and a reflux ratio of 2:1. After low boilers had been separated off, the temperature at the bottom was increased to 140-150° C. and the isononanal was taken off at the top (boiling point in ° C. at 100 hPa: 110-114° C.), while high boilers remained in the distillation bottoms.

The isononanal obtained had the following composition determined by gas chromatography and the following properties and was used for the subsequent liquid-phase oxidation.

TABLE 3

Gas-chromatographic analysis (% by area, in accordance with DIN 51405) of the isononanal starting out from 2-ethylhexanol

| First fraction/C8-hydrocarbons | 0.2 |
|---|---|
| Intermediate fraction | 0.4 |
| 2-Ethyl-4-methylhexanal | 10.8 |
| 2-Propyl-3-methylpentanal | 3.6 |
| 2,5-Dimethylheptanal | 21.9 |
| 2,3-Dimethylheptanal (isomer) | 4.8 |
| 2,3-Dimethylheptanal (isomer) + 2-ethylheptanal | 8.4 |
| 2-Methyloctanal | 1.7 |
| 3-Ethylheptanal | 10.4 |
| 4-Methyloctanal | 20.6 |
| 4,5-Dimethylheptanal | 0.6 |
| 6-Methyloctanal | 11.0 |
| Other i-nonanals | 1.8 |
| n-Nonanal | 0.9 |
| Final fraction | 2.9 |

TABLE 4

Properties of the isononanal starting out from 2-ethylhexanol

| Property/Unit | DIN/ASTM | Value |
|---|---|---|
| $V_{20}$ (mm$^2$/s) | D 445 | 1.536 |
| $V_{40}$ (mm$^2$/s) |  | 1.179 |
| Solidification point (° C.) |  | −100 |
| $d^{20/4}$ (g/cm$^3$) | DIN 51757, | 0.827 |
| $d^{50/4}$ (g/cm$^3$) | Meth. D/ASTM D 4052 | 0.811 |
| $n^{20/D}$ | DIN 51423-2/ ASTM D 1747 | 1.424 |
| CO number (mg KOH/g) | DIN 53173 | 339/349 |
| Flash point (° C.) | ISO 2719 | 60 |
| Hazen platinum/cobalt colour number | DIN ISO 6271/ ASTM D 1209 | 15 |

The liquid-phase oxidation of isononanal to isononanoic acid was carried out without addition of solvents in a bubble column reactor at 50° C. by means of pure oxygen at atmospheric pressure over a period of 6 hours. A 50% strength by weight aqueous solution of potassium hydroxide was added to the starting aldehyde in such an amount that 50 mmol of potassium were present per mol of isononanal.

The crude acid obtained was subsequently distilled in a 4.5 plate column at a temperature at the bottom of 148-159° C. and a temperature at the top of 136-139° C. at 20 hPa. Low boilers and unreacted aldehyde were separated off as first fraction and high boilers remained in the distillation residue. The distillation yield of isononanoic acid was 84.7% with a gas-chromatographically determined purity of 98.8%.

The isononanoic acid obtained had the following composition determined by gas chromatography in accordance with DIN 51405 (% by area):

TABLE 5

Gas-chromatographic analysis of the isononanoic acid starting out from 2-ethylhexanol (% by area, in accordance with DIN 51405)

| | |
|---|---|
| First fraction | 0.4 |
| 2-Ethyl-4-methylhexanoic acid | 9.3 |
| 2-Propyl-3-methylpentanoic acid | 3.0 |
| 2,5-Dimethylheptanoic acid + 2,3-dimethylheptanoic acid (isomer) | 25.7 |
| 2,3-Dimethylheptanoic acid (isomer) | 8.4 |
| 3-Ethylheptanoic acid + 2-ethylheptanoic acid | 12.9 |
| 2-Methyloctanoic acid | 0.8 |
| 4-Methyloctanoic acid | 20.9 |
| 6-Methyloctanoic acid | 12.3 |
| n-Nonanoic acid | 0.3 |
| Other i-nonanoic acids | 5.2 |
| Final fraction | 0.8 |

The properties determined for the isononanoic acid are shown in Table 6.

TABLE 6

Properties of the isononanoic acid starting out from 2-Ethylhexanol

| Property/Unit | DIN/ASTM | Value |
|---|---|---|
| $V_{20}$ (mm$^2$/s) | D 445 | 10.68 |
| $V_{40}$ (mm$^2$/s) | | 5.88 |
| $d^{20/4}$ (g/cm$^3$) | DIN 51757, Meth. D/ | 0.906 |
| $d^{50/4}$ (g/cm$^3$) | ASTM D 4052 | 0.883 |
| $n^{20/D}$ | DIN 51 423-2/ ASTM D 1747 | 1.432 |
| Solidification point (° C.) | | −81 |
| Boiling point (° C.) at 1013 hPa | DIN 53171/ ASTM D 1078 | 241-242 |
| Acid number mg KOH/g | DIN EN ISO 2114/ ASTM D 1613 | 351 |
| Flash point (° C.) | ISO 2719 | 129 |
| Hazen platinum/cobalt colour number | DIN ISO 6271/ ASTM D 1209 | 7 |

IV. Vinylation of the Isononanoic Acid Obtained in Step III.

The experimental set-up shown in FIG. 1 was used for carrying out Example IV./1 (continuous process) below.

The transvinylation reagent vinyl acetate was fed via line (1) and the isononanoic acid to be vinylated was fed via line (2) into a mixing vessel (3) from which the mixture was introduced via line (4) into the reaction vessel (5) configured as a flow tube. The liquid reaction output was introduced via line (6) into a depressurization vessel (7) in which depressurization to atmospheric pressure was carried out, optionally after prior cooling in the cooling apparatus (7') (shown as a broken line). Any gas phase formed in the depressurization operation was discharged via line (8) and the liquid phase formed was introduced via line (9) into the separation vessel (10). In the separation vessel (10), separation into a volatile fraction enriched in vinyl acetate, acetic acid and the desired vinyl isononanoate, which was combined via line (11) with any volatile components from the depressurization stage brought via line (8) and fed via line (12) to the separation vessel (13). The vinyl acetate separated off in the separation vessel (13) was recirculated via line (14) and combined with the vinyl acetate brought via line (1). The acetic acid formed during the transvinylation reaction and obtained in the separation vessel (13) and also the desired vinyl isononanoate were discharged via line (15) and introduced into the separation vessel (16) from which the acetic acid formed was taken off via line (17) and the desired vinyl isononanoate was taken off via line (18). The vinyl isononoate obtained could subsequently be purified further (not shown in FIG. 1).

The liquid output discharged via line (9) was analysed by gas chromatography. The conversions, selectivities and yields determined from the analytical data and the space-time yield of vinyl isononanoate calculated therefrom are summarized in Table 7 below. The reaction conditions set in the reaction vessel (5) are likewise indicated.

The less volatile fraction which was obtained in the separation vessel (10) and contained the unreacted isononanoic acid together with the transvinylation catalyst was discharged via line (19) and, optionally after discharge of a high boiler-containing side stream via line (20) (shown as a broken line), recirculated as catalyst recycle via line (21).

The catalyst solution was prepared by mixing the catalyst precursor palladium acetate Pd(OAc)$_2$ with the bidentate, nitrogen-containing ligand 1,10-phenanthroline in a mixture of vinyl acetate and isononanoic acid and supplemented via line (22). The resulting mixture of old and fresh catalyst was subsequently fed via line (23) into the mixing vessel (3).

TABLE 7

Conditions and results of the continuous preparation of vinyl isononanoate in the flow tube

| | Example No. IV./1 |
|---|---|
| Residence time [min] | 75 |
| Reactor volume [ml] | 200 |
| Temperature [° C.] | 140 |
| Pressure [MPa] | 2 |
| Molar ratio of carboxylic acid:vinyl acetate:catalyst precursor | 1.0:5.0:0.0010 |
| Molar ratio of catalyst precursor:ligand | 1:8 |
| Catalyst precursor | Pd(OAc)$_2$ |
| Ligand | 1,10-Phenanthroline |
| Carboxylic acid [g/h] | 39.6 |
| Vinyl acetate [g/h] | 107.8 |
| Catalyst precursor [mg/h] | 56.2 |
| Ligand [mg/h] | 361.1 |
| Conversion [%] | 77.2 |
| Yield [%] | 76.7 |
| Selectivity [%] | 99.3 |
| Space-time yield [g/l · h] | 177 |

The vinyl ester mixture obtained was subsequently distilled in a 4.5 plate column at a temperature at the bottom of 86-160° C. and a temperature at the top of 68-95° C. at 5-500 hPa. Acetic acid and unreacted vinyl acetate were separated off as first fraction and the unreacted isononanoic acid, the palladium complex and free ligand remain in the distillation residue.

The vinyl isononanoate obtained had the following composition determined by gas chromatography in accordance with DIN 51405 (% by area):

TABLE 7a

Gas-chromatographic analysis of the vinyl isononanoate starting out from 2-ethylhexanol (% by area, in accordance with DIN 51405)

| | |
|---|---|
| First fraction | 0.0 |
| Intermediate fraction | 0.1 |
| Vinyl 2-ethyl-4-methylhexanoate | 7.3 |
| Vinyl 2-propyl-3-methylpentanoate | 2.3 |
| Vinyl 2,3-dimethylheptanoate + vinyl 2,5-dimethylheptanoate | 44.5 |
| Vinyl 3-ethylheptanoate | 16.6 |

TABLE 7a-continued

Gas-chromatographic analysis of the vinyl isononanoate starting out from 2-ethylhexanol (% by area, in accordance with DIN 51405)

| | |
|---|---|
| Vinyl 4-methyloctanoate | 17.4 |
| Vinyl 6-methyloctanoate | 3.9 |
| Positional isomers of aliphatic vinyl esters | 7.9 |
| Final fraction | 0 |

The properties determined for the vinyl isononanoate are shown in Table 7b.

TABLE 7b

Properties of the vinyl isononanoate starting out from 2-ethylhexanol

| Property/Unit | DIN/ASTM | Value |
|---|---|---|
| $V_{20}$ (mm$^2$/s) | D 445 | 1.735 |
| $V_{40}$ (mm$^2$/s) | | 1.271 |
| $d^{20/4}$ (g/cm$^3$) | DIN 51757, Meth. D/ | 0.8776 |
| $d^{50/4}$ (g/cm$^3$) | ASTM D 4052 | 0.8516 |
| $n^{20/D}$ | DIN 51 423-2/ ASTM D 1747 | 1.4323 |
| Solidification point (° C.) | | −100 |
| Acid number (mg KOH/g) | DIN EN ISO 2114/ ASTM D 1613 | 0.57 |
| Flash point (° C.) | ISO 2719 | 77 |
| Hazen platinum/cobalt colour number | DIN ISO 6271/ ASTM D 1209 | 6 |

Examples IV./2-4 below were carried out batchwise in a closed reaction vessel. The isononanoic acid prepared as per step III., vinyl acetate, catalyst precursor and ligand were placed in a 1 l autoclave. The autoclave was stirred at 600 revolutions per minute and brought to the reaction temperature indicated in each case. A pressure of 2 MPa was set by injection of nitrogen.

After the reaction time indicated, the batch was allowed to cool and depressurized to atmospheric pressure. The reaction mixture obtained was analysed by gas chromatography and the conversion of isononanoic acid and also the selectivity and yield of vinyl isononanoate were determined. The reaction conditions and results of the batchwise preparation of vinyl isononanoate are shown in Table 8 below.

TABLE 8

Conditions and results of the batchwise preparation of $C_9$-vinyl esters in an autoclave

| | Example No. | | |
|---|---|---|---|
| | IV./2 | IV./3 | IV./4 |
| Reaction time [min] | 90 | 120 | 180 |
| Temperature [° C.] | 130 | 140 | 100 |
| Molar ratio of C9-acid:vinyl acetate:catalyst precursor | 1.0:3.0:0.00125 | 1.0:6.0:0.00200 | 1.0:5.0:0.00125 |
| Molar ratio of catalyst precursor:ligand | 1:5 | 1:8 | 1:5 |
| Catalyst precursor | Pd(OAc)$_2$ | Pd(OAc)$_2$ | Pd(OAc)$_2$ |
| Ligand | 1,10-Phenanthroline | 2,2'-Bipyridyl | 1,10-Phenanthroline |
| C9 acid [g] | 122.1 | 75.7 | 86.7 |
| Vinyl acetate [g] | 199.3 | 247.2 | 235.9 |
| Catalyst precursor [mg] | 211.6 | 214.9 | 153.8 |
| Ligand [mg] | 869.2 | 1196.2 | 617.2 |
| Conversion [%] | 79.5 | 83.1 | 49.8 |

TABLE 8-continued

Conditions and results of the batchwise preparation of $C_9$-vinyl esters in an autoclave

| | Example No. | | |
|---|---|---|---|
| | IV./2 | IV./3 | IV./4 |
| Yield [%] | 78.9 | 82.2 | 49.4 |
| Selectivity [%] | 99.2 | 98.9 | 99.1 |

V. Vinylation of an Acid Mixture Containing Tertiary Isononanoic Acids

An acid mixture containing tertiary isononanoic acids which was obtained from the Koch reaction as described in J. Falbe, Carbon Monoxide in Organic Synthesis, Springer Verlag Berlin, Heidelberg, N.Y., 1970, pages 127-135 using the abovementioned octene starting mixture from step I. and had the following composition determined by gas chromatography (% by area, in accordance with DIN 51405) was used for the transvinylation below:

| | |
|---|---|
| First fraction + C8-olefins | 0.1 |
| Octene oligomers | 0.1 |
| Intermediate fraction | 0.1 |
| 2,2-Dimethylheptanoic acid | 13.1 |
| 2-Ethyl-2-methylhexanoic acid | 81.5 |
| Positional isomers of aliphatic isononanoic acids | 4.8 |
| Final fraction | 0.3 |

The experimental set-up as described in Example IV./1 was used. The conversions, selectivities and yields determined from the analytical data and also the space-time yield of vinyl isononanoate calculated therefrom are summarized in Table 9 below. The reaction conditions set in the reaction vessel are likewise indicated.

TABLE 9

Conditions and results of the continuous transvinylation of a mixture containing tertiary isononanoic acids in the flow tube

| | Example No. IV./5 |
|---|---|
| Residence time [min] | 60 |
| Reactor volume [ml] | 200 |
| Temperature [° C.] | 140 |
| Pressure [MPa] | 2 |
| Molar ratio of carboxylic acid:vinyl acetate:catalyst precursor | 2.0:1.0:0.00244 |
| Molar ratio of catalyst precursor:ligand | 1:3 |
| Catalyst precursor | Pd(OAc)$_2$ |
| Ligand | 1,10-Phenanthroline |
| Carboxylic acid [g/h] | 142.5 |
| Vinyl acetate [g/h] | 38.8 |
| Catalyst precursor [mg/h] | 246.7 |
| Ligand [mg/h] | 594.0 |
| Conversion [%][a] | 80.7 |
| Yield [%][a] | 70.0 |
| Selectivity [%] | 86.8 |
| Space-time yield [g/l · h] | 291 |

[a]Conversion and yield based on vinyl acetate

The vinyl ester mixture obtained was subsequently distilled in a 9.0 plate column at a temperature at the bottom of 75-140° C. and a temperature at the top of 34-114° C. at 10-1013 hPa. Acetic acid and unreacted vinyl acetate were separated off as first fraction and the unreacted tertiary isononanoic acids, the palladium complex and free ligand remain in the distillation residue.

The vinyl ester mixture obtained had, according to gas-chromatographic analysis (% by area, in accordance with DIN 51405), a purity of 99.7%; the balance to 100% consists of first fraction and final fraction components. The vinyl ester mixture (99.7%) consists mainly of the isomers vinyl 2-ethyl-2-methyl-hexanoate (90.4%) and vinyl 2,2-dimethylheptanoate (4.8%) and as balance up to 99.7% further vinyl esters of positionally isomeric isononanoic acids. The properties determined for the vinyl isononanoate are shown in Table 10.

TABLE 10

Properties of the vinyl isononanoate from the continuous transvinylation of a mixture containing tertiary isononanoic acids

| Property/Unit | DIN/ASTM | Value |
|---|---|---|
| $V_{20}$ (mm$^2$/s) | D 445 | 1.752 |
| $d^{20/4}$ (g/cm$^3$) | DIN 51757, Meth. D/ ASTM D 4052 | 0.8776 |
| $n^{20/D}$ | DIN 51 423-2/ ASTM D 1747 | 1.4313 |
| Acid number (mg KOH/g) | DIN EN ISO 2114/ ASTM D 1613 | 0.046 |
| Hazen platinum/cobalt colour number | DIN ISO 6271/ ASTM D 1209 | 13 |

The invention claimed is:

1. Process for preparing the vinyl ester of isononanoic acid starting out from 2-ethylhexanol, characterized in that
   (a) 2-ethylhexanol is dehydrated in the presence of a catalyst to form octene;
   (b) the octene obtained in step a) is converted into an isononanoic acid having one more carbon atom; and
   (c) the isononanoic acid obtained in step b) is converted into the corresponding vinyl ester.

2. Process according to claim 1, characterized in that aluminium oxide, nickel deposited on aluminium oxide, or phosphoric acid deposited on silicon dioxide or aluminium oxide is used as catalyst in step a).

3. Process according to claim 1, characterized in that 2-ethylhexanol is dehydrated in the gas phase in step a).

4. Process according to claim 1, characterized in that, in step b), the octene is reacted with carbon monoxide and hydrogen in the presence of a transition metal compound of group VIII of the Periodic Table of the Elements to form isononanal and subsequently oxidized to isononanoic acid.

5. Process according to claim 4, characterized in that a cobalt compound or rhodium compound is used as transition metal compound of group VIII of the Periodic Table of the Elements in step b).

6. Process according to claim 4, characterized in that the isononanal is distilled in step b).

7. Process according to claim 4, characterized in that isononanal is oxidized to isononanoic acid in the presence of alkali metal or alkaline earth metal carboxylates in step b).

8. Process according to claim 7, characterized in that lithium isononanoate, potassium isononanoate, sodium isononanoate, calcium isononanoate or barium isononanoate is used as alkali metal or alkaline earth metal carboxylate.

9. Process according to claim 4, characterized in that isononanal is oxidized to isononanoic acid by means of oxygen or oxygen-containing gases in step b).

10. Process according to claim 1, characterized in that the octene is reacted with carbon monoxide in the presence of water to form isononanoic acid in step b).

11. Process according to claim 1, characterized in that the isononanoic acid is reacted with acetylene to form the vinyl ester in step c).

12. Process according to claim 11, characterized in that the reaction of the isononanoic acid with acetylene is carried out in the presence of zinc salts.

13. Process according to claim 1, characterized in that the isononanoic acid is reacted with a vinyl ester of another carboxylic acid in step c).

14. Process according to claim 13, characterized in that the isononanoic acid is reacted with vinyl acetate or vinyl propionate in step c).

15. Process according to claim 14, characterized in that the acetic acid liberated in the reaction of isononanoic acid with vinyl acetate is used for preparing vinyl acetate, acetate esters, acetyl halides, amides, carboxylic anhydrides, chloroacetic acids or ethanol.

16. Process according to claim 2, characterized in that 2-ethylhexanol is dehydrated in the gas phase in step a).

17. Process according to claim 2, characterized in that, in step b), the octene is reacted with carbon monoxide and hydrogen in the presence of a transition metal compound of group VIII of the Periodic Table of the Elements to form isononanal and subsequently oxidized to isononanoic acid.

18. Process according to claim 17, characterized in that a cobalt compound or rhodium compound is used as transition metal compound of group VIII of the Periodic Table of the Elements in step b).

19. Process according to claim 2, characterized in that, in step b) the octene is reacted with carbon monoxide in the presence of water to form isononanoic acid.

* * * * *